United States Patent
Falcone, Jr.

Patent Number: 6,065,490
Date of Patent: May 23, 2000

[54] RETRACTABLE OXYGEN SUPPLY HOSE MECHANISM FOR MEDICAL OXYGEN THERAPY DEVICES AND MEDICAL OXYGEN TREATMENT DEVICES

[76] Inventor: Vincent F Falcone, Jr., P.O. Box 1210, Amite, La. 70422

[21] Appl. No.: 09/135,422

[22] Filed: Aug. 17, 1998

[51] Int. Cl.[7] .................................................. B65H 75/34
[52] U.S. Cl. .............................. 137/355.23; 137/355.21; 128/201.27
[58] Field of Search ............................. 137/355.23, 355.2, 137/355.21, 355.22; 128/201.27, 204.26, 201.28; 604/159; 242/371, 388.9

[56] References Cited

U.S. PATENT DOCUMENTS

| | | | |
|---|---|---|---|
| 1,389,314 | 8/1921 | McMullin | 137/355.23 |
| 1,453,999 | 5/1923 | Royer | 137/355.21 |
| 1,675,140 | 6/1928 | Schenderlein | 137/355.23 |
| 2,629,630 | 2/1953 | Roark | 137/355.21 |
| 2,711,734 | 6/1955 | Moe | 604/159 |
| 3,361,155 | 1/1968 | Whitfield | 137/355.23 |
| 3,995,628 | 12/1976 | Gula et al. | 604/159 |
| 4,022,201 | 5/1977 | Diggs | 128/201.27 |
| 4,342,313 | 8/1982 | Chittenden | 604/159 |
| 4,713,059 | 12/1987 | Bickelhaupt et al. | 604/159 |
| 5,119,843 | 6/1992 | Keenan | 137/355.23 |
| 5,351,906 | 10/1994 | Feathers | 242/371 |
| 5,402,551 | 4/1995 | Workhoven et al. | 137/355.26 |
| 5,450,874 | 9/1995 | Hamula | 137/355.23 |
| 5,826,608 | 10/1998 | Pierce | 137/355.23 |

*Primary Examiner*—Denise L. Ferensic
*Assistant Examiner*—Joanne Y. Kim

[57] ABSTRACT

The modification of a spring loaded retractable mechanism currently used for wire to facilitate the quick dispensing and retraction of an oxygen supply hose for medical oxygen therapy and medical oxygen treatment devises. An adaptor is developed to permit the adaptor to be connected to a supply hose reel top surface. The adaptor permits the patient supply hose to be attached to a swivel connector that is fixed to the adaptor cap. The adaptor facilitates the free movement of the adaptor and the supply hose reel to prevent binding or impingement of the patient supply hose.

4 Claims, 2 Drawing Sheets

RETRACTABLE OXYGEN SUPPLY HOSE MECHANISM FOR MEDICAL OXYGEN THERAPY DEVICES AND MEDICAL OXYGEN TREATMENT DEVICES

BACKGROUND OF THE INVENTION

This invention relates to the modification of a spring loaded retractable mechanism designed for the use of storing electrical wire to facilitate, by the attachment of a newly invented adaptor, the storage and quick release of oxygen supply hose that is used for Medical Oxygen supply, therapy, or treatments. Medical Oxygen supply hoses do range in lengths from 25 to 50 feet long. The hoses which connect the supply or treatment apparatus to the patient can present a hazard by cluttering up walk space. The therapist needlessly losses time by tying up the excess length of hose only to be faced with the problem of the hose that remains between therapies. This spring loaded retractable device permits the quick release of the required length of oxygen supply hose and the quick return to storage within the unit by a simple tug on the hose.

BRIEF SUMMARY OF THE INVENTION

This invention is designed to modify a spring loaded retractable mechanism presently utilized for the dispensing and storing of electrical wire for use with medical oxygen supply hose. The supply hose that goes to the patient can be stored on a hollow supply spool which is disposable.

It permits the release and retraction of exactly the amount of supply hose needed, up to a length of 50 feet. It incorporates the use of a newly developed adaptor that facilitates the turning of the spool without the twisting or the binding of the supply hose.

DETAILED DESCRIPTION OF THE INVENTION

Figure 1:
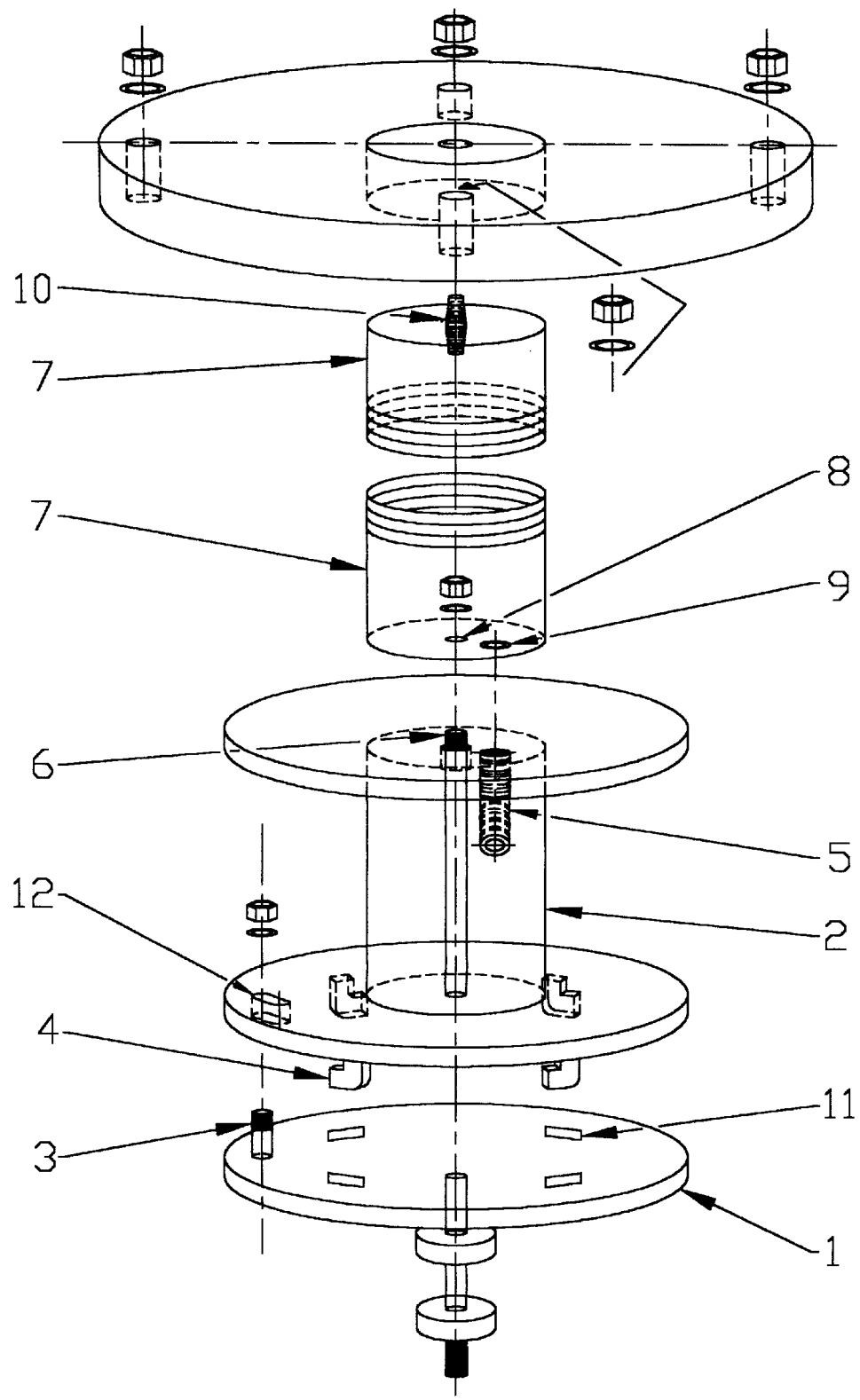
FIG. 1 is frontal view of the modifications to the permanent spring loaded disc, the modifications to the patient oxygen supply spool, and the newly developed adaptor with the incorporated SalterOxygen Tubing Swivel Connector by Salter Labs, 100 W. Sycamore Road, Arvin, Calif. 93203.

Referring to FIG. 1, This invention is designed to modify a spring loaded retractable storage device for electrical wiring and adapt it by the attachment of a simple device for the storage of medical oxygen supply hoses. The base of the spring loaded mechanism remains as a two-reel device with a spring attached from the smaller reel to the base axis of the larger reel indicated at 1, a simple plastic disc with four grooves that will permit the attachment of the supply hose reel indicated at 2. The flat disc base has a small bolt at arrow 3, located on the peripheral which will insert into the groove of the supply hose reel. The supply hose reel has four plastic winged-shaped tabs at arrow 4, that permit the reel to be fitted onto grooves of the base disc at 11 and turned until locked. The bolt of the lower disc fits into a small groove in the supply reel disc and a nut secures the two firmly together.

The Supply reel disc is a modification of the wire supply reel spool. The modification is the elimination of the circular copper metal strips on the top of the spool that attaches to the two poles of the electrical wire on the interior of the spool. The oxygen supply hose is then facilitated by a hole at arrow 5, from the hollow interior through the upper surface of the top disc medially. A metal center axis indicated at 6, begins at the spools base through the hollow core and permeates through the upper disc with an amount exposed that is threaded and will permit a lock washer and nut.

A newly developed adaptor indicated at 7, attaches to the upper disc surface. It prevents the twisting or binding of the patients supply hose when the reel turns. The adaptor is a simple plastic cylinder that resembles a medicine bottle. It has a small hole in its base at arrow 8 that permits the metal axis to bolt it firmly to upper supply hose spool disc surface. There is a second hole in the base at 9, located medially through which the patient supply hose penetrates. The cylinder is in two parts with the bottom threaded and the top part died. The top part (cap) has a Salter Oxygen Tubing Swivel Connector at 10, molded into its axis with the upper portion of the swivel remaining fixed. The patient supply hose connects to the rotatable portion of the swivel located interiorly where by the supply hose may be unwound and retracted in an untangled manner, and the cylinder cap can now be screwed to the cylinder base.

Figure 2:
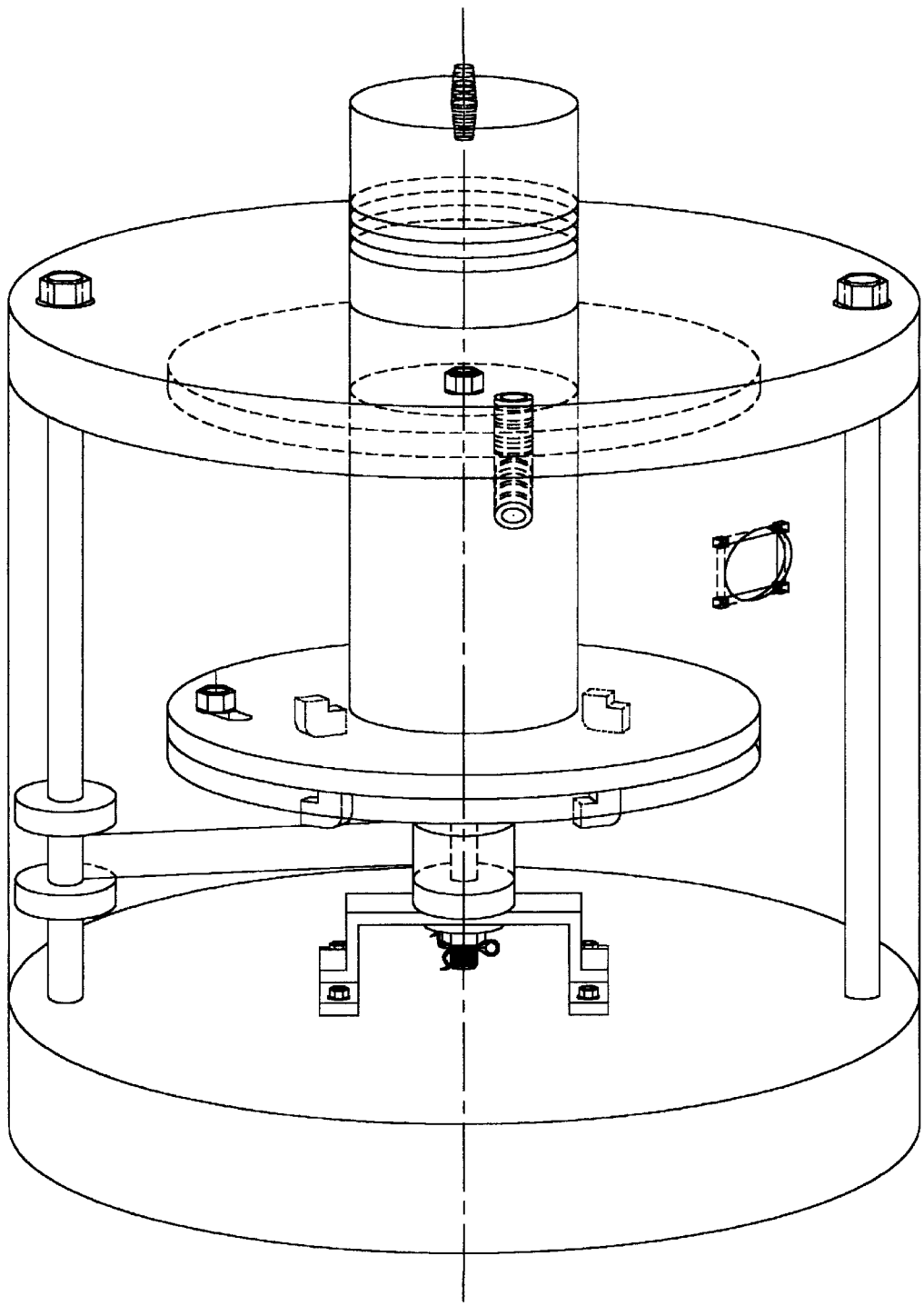
FIG. 2 is a view of the closed housing with the newly developed adaptor protruding from the center of the top housing and the optionally used base mounting plate.

The final modification to consider is the housing in FIG. 2. The cover of the housing has a centrally located hole that will permit the cylindrical adaptor to turn freely. The cover is bolted to the housing bottom. The device permits the removal and disposal of the supply hose mechanism while permitting the reuse of the spring loaded retractable mechanism portion.

I claim:

1. A hose reel mechanism comprising a replaceable spool for medical oxygen supply for treatment or therapy comprising:

a spring loaded retractable mechanism having a large reel and a small reel and a retractable spring wherein, said small reel and an axis of said large reel are connected by said retractable spring;

said replaceable spool comprising an upper and a lower discs being attached by a cylinder in between said discs, and an adaptor, at least one tab extending from said lower disc being insertable into at least one groove of said large reel removeably attaching said replaceable spool to said spring loaded retractable mechanism;

a supply hose wound around said cylinder of said spool, an upstream end of said supply hose being connected to a swivel connector in said adaptor via a hole in said cylinder for providing said medical oxygen supply.

2. A hose reel as recited in claim 1 wherein said lower disc includes four winged shaped tabs which are fitted onto four grooves of said large disc.

3. A hose reel as recited in claim 1 wherein said adaptor includes two members threaddedly connected to one another.

4. A hose reel as recited in claim 1 wherein said supply hose is attached to a rotatable portion of said swivel connector located a within said adaptor and a fluid source is attached to the other side of said rotatable portion of said swivel connector located externally, whereby said supply hose may be unwound and retracted in an untangled manner.

\* \* \* \* \*